(12) United States Patent
Otsuka et al.

(10) Patent No.: US 7,309,311 B2
(45) Date of Patent: Dec. 18, 2007

(54) ENDOSCOPIC OBSERVATION APPARATUS AND MEDICAL DEVICE HOLDER

(75) Inventors: Satoshi Otsuka, Mitaka (JP); Toru Shinmura, Hachioji (JP); Tomoaki Yamashita, Hachioji (JP); Kenji Hirose, Hachioji (JP); Hisao Isobe, Hachioji (JP); Masaaki Ueda, Sagamihara (JP)

(73) Assignee: Olympus Corporation (JP)

( * ) Notice: Subject to any disclaimer, the term of this patent is extended or adjusted under 35 U.S.C. 154(b) by 481 days.

(21) Appl. No.: 10/850,660

(22) Filed: May 21, 2004

(65) Prior Publication Data
US 2004/0267089 A1 Dec. 30, 2004

(30) Foreign Application Priority Data
May 21, 2003 (JP) ............................. 2003-143381
Apr. 30, 2004 (JP) ............................. 2004-136204

(51) Int. Cl.
*A61B 1/04* (2006.01)
(52) U.S. Cl. ...................... 600/112; 600/102; 600/167; 600/168
(58) Field of Classification Search ............... 600/102, 600/112, 131, 168, 167; 606/130
See application file for complete search history.

(56) References Cited
U.S. PATENT DOCUMENTS 5,273,039 A * 12/1993 Fujiwara et al. ............ 600/407
5,951,461 A * 9/1999 Nyo et al. .................. 600/118
6,083,151 A * 7/2000 Renner et al. .............. 600/114
6,346,072 B1 * 2/2002 Cooper ........................ 600/102
6,821,243 B2 * 11/2004 Pagliuca et al. ............ 600/102
7,035,716 B2 * 4/2006 Harris et al. ................ 700/245
2002/0022764 A1 * 2/2002 Smith et al. ................. 600/114
2004/0210106 A1 * 10/2004 Banju ......................... 600/102

FOREIGN PATENT DOCUMENTS

| JP | 8-52158 | 2/1996 |
|---|---|---|
| JP | 8-206059 | 8/1996 |
| JP | 9-149877 | 6/1997 |

OTHER PUBLICATIONS

Information Sheet dated May 14, 2004 prepared by Client with explanation of relevancy of the cited prior art.

* cited by examiner

*Primary Examiner*—John P Leubecker
(74) *Attorney, Agent, or Firm*—Ostrolenk, Faber, Gerb & Soffen, LLP

(57) ABSTRACT

An endoscope is connected optically removably to a TV camera through an adapter. A plurality of fixing pins is arranged on both sides of an insertion axis of an insertion part of the endoscope. A fixing unit to fix the endoscope removably is provided at the front end of an arm unit of an endoscope holder which supports the endoscope movably. The fixing unit has a claw and a movable claw, and grips the fixing pins of the endoscope releasably between the claw and the movable claw.

10 Claims, 11 Drawing Sheets

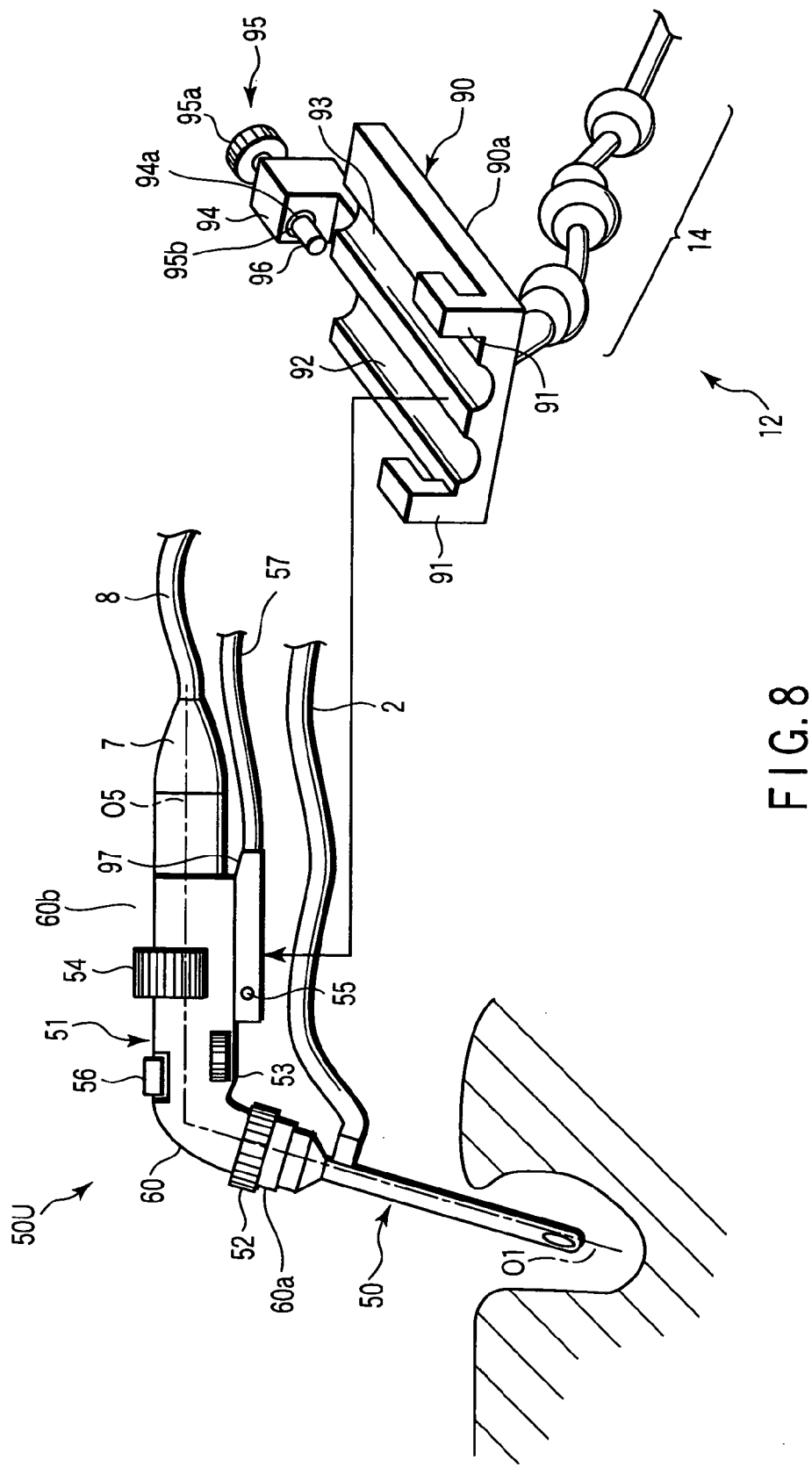
F I G. 8

ENDOSCOPIC OBSERVATION APPARATUS AND MEDICAL DEVICE HOLDER

CROSS-REFERENCE TO RELATED APPLICATIONS

This application is based upon and claims the benefit of priority from prior Japanese Patent Applications No. 2003-143381, filed May 21, 2003; and No. 2004-136204, filed Apr. 30, 2004, the entire contents of both of which are incorporated herein by reference.

BACKGROUND OF THE INVENTION

1. Field of the Invention

The present invention relates to an endoscopic observation apparatus and a medical device holder used in the medical field, for example, neurosurgery, by inserting an endoscope into a body cavity.

2. Description of the Related Art

Generally, medical instruments such as an endoscope and treatment tool are sometimes used in being held by a holder. For example, Jpn. Pat. Appln. KOKAI Publication No. 8-52158 (patent document 1) discloses an articulated holder arm which can hold medical instruments such as an endoscope and treatment tool. This holder arm has a plurality of arms, a joint between the arms, and a brake means to switch the joint to a fixed state and a released movable state. A grip is provided at the front end of the holder. The grip holds and fixes the outer circumference of medical instruments such as an endoscope and treatment tool. When the brake means is switched to the released state, each arm of the multi-joint arm structure becomes movable in three dimensions. Thus, the medical instrument motion is adjusted in three dimensions through the holder. By switching the brake means to the fixed position in the state that the instrument is being inserted into a desired part, each arm is fixed at its moved position.

Further, Jpn. Pat. Appln. KOKAI Publication No. 9-149877 (patent document 2) discloses an endoscope holder to hold an endoscope. The endoscope disclosed here has a thick part connected to the base end of a slender insertion part which is inserted into the tube cavity. In the endoscope holder of the patent document 2, an endoscope attachment is provided at the front end of the endoscope holder which is movable in three dimensions. This attachment has a substantially cylindrical insertion hole to insert the insertion part of the endoscope, and an endoscope fixing screw. The insertion hole is shaped to meet the outside shape of the thick part of the endoscope. The endoscope holder is constructed to press and fix the endoscope to the attachment by tightening the fixing screw after the thick part is inserted into the insertion hole of the attachment.

Further, Jpn. Pat. Appln. KOKAI Publication No. 8-206059 (patent document 3) discloses an endoscope holder with the structure different from the unit of the patent document 2. This endoscope holder contains an image pickup optics to pick up an image observed through an endoscope, and a variable magnification optics to change the magnification of a pickup image. An attachment provided at the rear end of the endoscope is connected removably to the front end of the holder. The holder is further provided with an endoscope attachment, which is attached optically removably to the optics of the endoscope. At the front end of the holder, a plurality of controls are arranged to adjust and change the direction, magnification and focal position of an observation image.

BRIEF SUMMARY OF THE INVENTION

According to an aspect of the present invention, there is provided an endoscopic observation apparatus comprising:

an endoscopic observation unit comprising an endoscope which has an insertion part having a distal end, a base end and an insertion axis, and inserted into a body cavity, and an observation unit arranged at the distal end, the observation unit having an observation optical axis extended in the insertion direction of the insertion part;

an adaptor which is fit removably to the base end of the endoscope; and an image pickup camera which is fixed to the endoscope through the adapter, and picks up an image obtained by the observation unit of the endoscope through the adapter, the camera having an image pickup optical axis;

wherein the endoscope, adapter and image pickup camera are combined;

a plurality of fixed parts which is arranged substantially axially symmetrical on both sides of the endoscopic observation unit, the fixed parts arranged at least in one of the endoscope and adapter;

a holder which has a fixing unit to fix removably the fixed parts, and a support unit to support the endoscopic observation unit movably; and a grip which is provided in the fixing unit and grips the fixed parts releasably, the grip extended to both sides of the endoscopic observation unit.

According to a second aspect of the present invention, there is provided an endoscopic observation apparatus comprising:

an endoscope which has an insertion part to be inserted into a body cavity, and an observation unit connected to the endoscope;

a fixed part which is provided in the endoscopic observation unit;

a holder which has a fixing unit to fix the fixed part removably, and a support unit to support the endoscopic observation unit movably; and an attach-detach part which is provided in a connector to connect the fixed part and fixing unit, and attach and detach the fixed part to/from the fixing unit by moving in the insertion direction of the insertion part of the endoscope.

According to a third aspect of the present invention, there is provided a medical device holder comprising:

a holding unit which is connected removably with a medical device having an insertion part to be inserted into a body cavity;

a support unit which supports the holding unit locatable and fixable at free three-dimensional positions; and a base unit which has a fixing unit to fix the support unit to the floor;

wherein an attach-detach part which attaches and detaches a medical device to/from the support unit by moving the medical device in the direction substantially identical to the insertion direction of the medical device when attaching and detaching the medical device to/from the support unit, is provided.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the embodiments given below, serve to explain the principles of the invention.

FIG. 8 is a schematic configuration of an essential part of an endoscopic observation apparatus according to a third embodiment of the present invention;

DETAILED DESCRIPTION OF THE INVENTION

Embodiment 1

Figure 1:
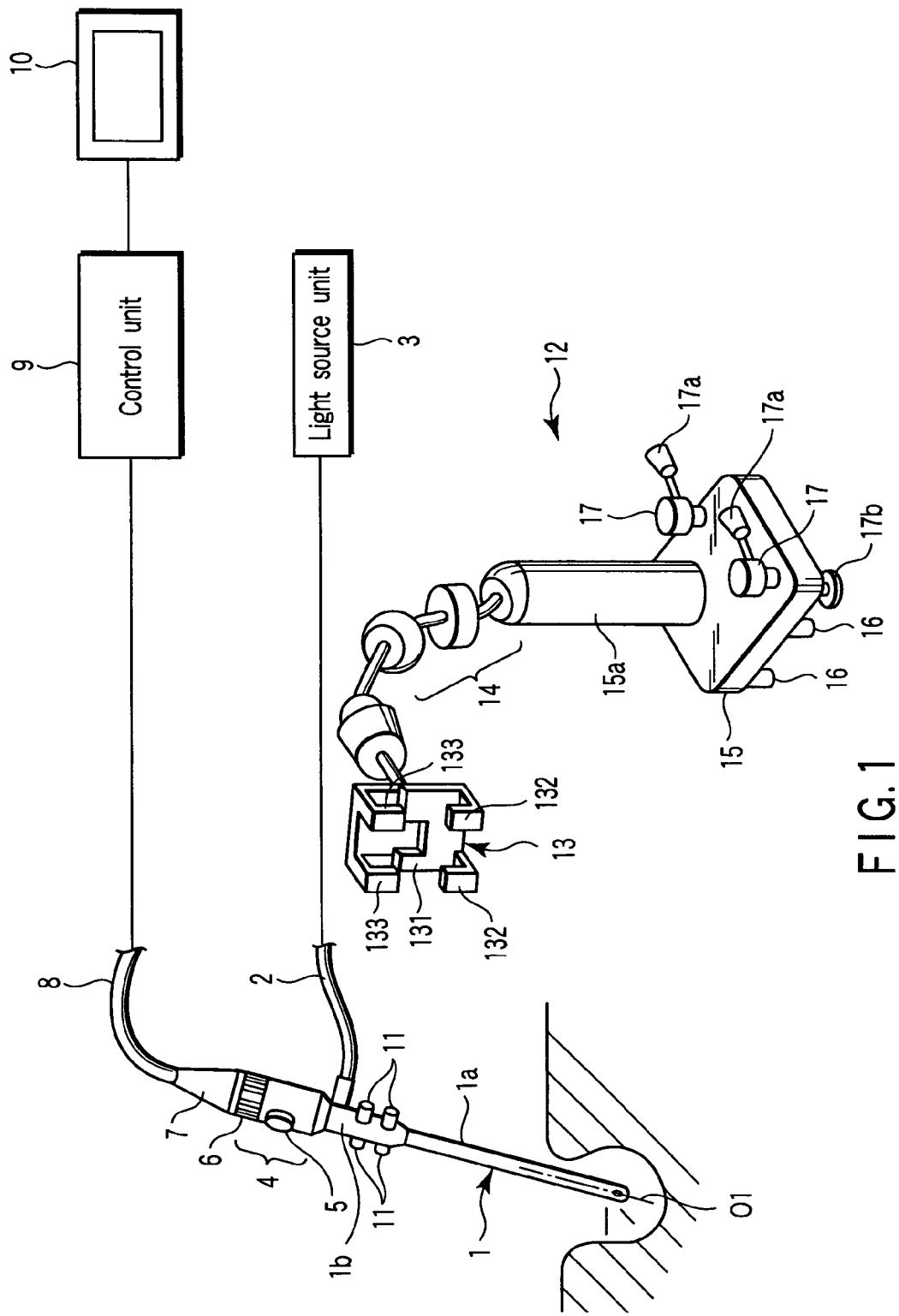
FIG. 1 is a schematic configuration of the whole endoscopic observation apparatus according to a first embodiment of the present invention.

A first embodiment of the present invention will be explained in detail hereinafter with reference to FIG. 1 to FIG. 3B. FIG. 1 shows a schematic configuration of the whole endoscopic observation apparatus according to the first embodiment. In FIG. 1, a reference numeral 1 denotes an endoscope constituting an observation means. The endoscope 1 has a slender insertion part 1a to be inserted into a body cavity. The insertion part 1a has a linear insertion axis O1 at the center of axis. The insertion part 1a contains a not-shown objective optics and relay optics. The base end of the insertion part 1a is connected with a thick part 1b. One end of a light guide 2 is connected removably to the thick part 1b. The other end of the light guide 2 is connected to a light source unit 3. With this structure, the illumination light from the light source unit 3 is supplied to the endoscope 1 through the light guide 2 to light a desired observation part.

One end of a television (TV) adapter 4 is connected removably to the thick part 1b of the endoscope 1. The adapter 4 is provided with a focus dial 5 for focal adjustment described later in detail, and a zoom dial 6 for zooming. The rotating directions of the focus dial 5 and zoom dial 6 are arranged substantially orthogonal to the adapter 4.

A television (TV) camera 7 or an image pickup camera is connected optically removably to the other end of the adapter 4. The TV camera 7 is connected to a control unit 9 through a cable 8. The control unit 9 is connected with a monitor 10. Thus, an observation image taken in through the endoscope 1 is picked up by the TV camera 7 through the adapter 4, and converted into an electric signal. Based on this electric signal, a video signal is generated in the control unit 9, and displayed on the monitor 10.

Figure 2:
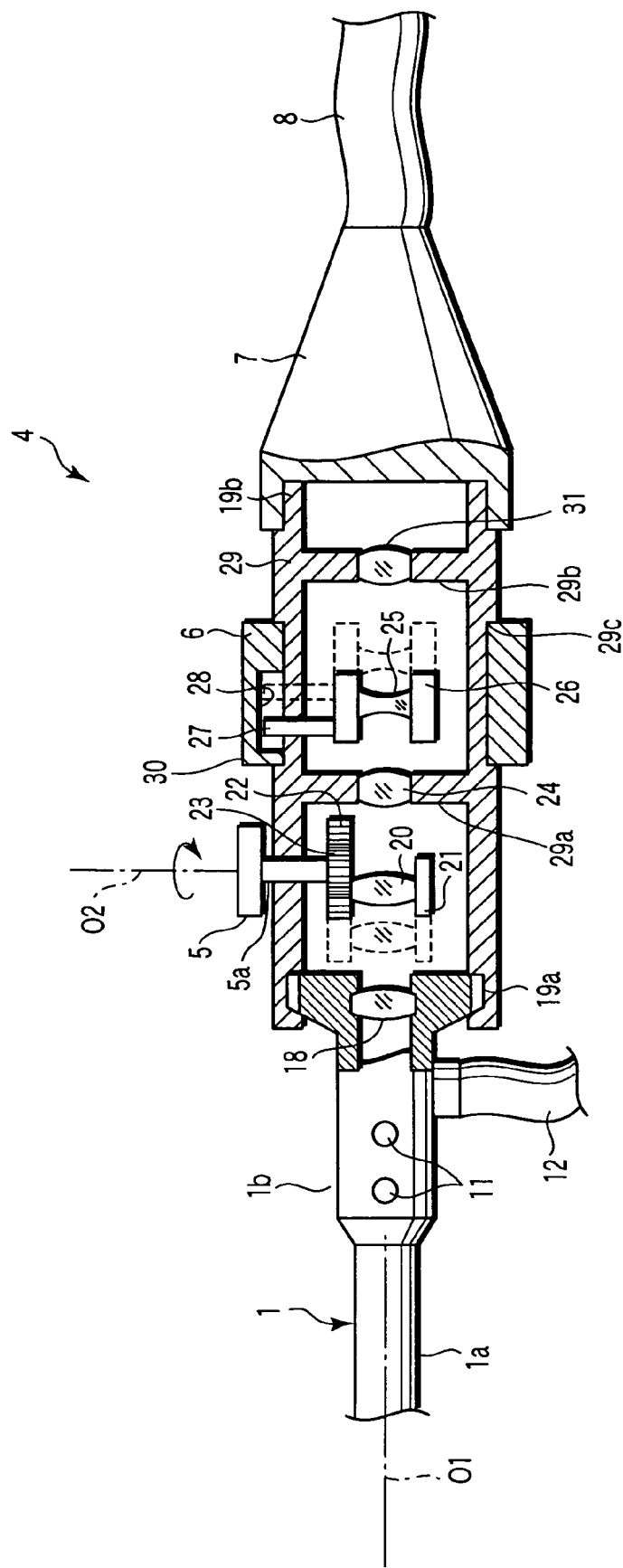
FIG. 2 is a side view, partially cross sectioned, of the internal structure of an adapter of the endoscopic observation apparatus of the first embodiment.

FIG. 2 shows the internal structure of the adapter 4. The adapter 4 has a substantially cylindrical main body 29. An endoscope attachment 19a is provided at one end of the main body 29, and a camera attachment 19b is provided at the other end. The base end of the thick part 1b of the endoscope 1 is connected removably to the endoscope attachment 19a.

The base end of the thick part 1b of the endoscope 1 contains an eyepiece 18. The main body 29 of the adapter 4 contains a focus lens 20 at the position corresponding to the eyepiece 18. The focus lens 20 is fixed to a movable frame 21. The movable frame 21 is provided with a rack 22 projected parallel to the insertion axis O1 of the endoscope 1.

On the outer circumference of the main body 29, a shaft 5a of the focus dial 5 is supported pivotally. The axis 5a is movable rotationally around the axis O2 substantially orthogonal to the insertion axis O1 of the endoscope. A gear 23 is fixed to the internal end of the axis 5a. The gear 23 engages with the rack 22. Thus, when the focus dial 5 is rotated around the axis O2, the gear 23 is rotated. In this time, the rack 22 engages with the gear 23, and the moves parallel to the insertion axis O1 of the endoscope 1. By this action, the movable frame 21 moves together with the rack 22 as one body, and the focus lens 20 is moved parallel to the axis O1.

At the center of the main body 29, a first zoom lens 24, a second zoom lens 25, and an image-forming lens 31 are provided. These first zoom lens 24, second zoom lens 25 and image-forming lens 31 are arranged on the same line as the optical axis of the focus lens 20.

The first zoom lens 24 is fixed to a first fixed frame 29a fixed to the inside wall of the main body 29. The first fixed frame 29a is arranged at almost the middle of the center axis of the main body 29. Similarly, the image-forming lens 31 is fixed to a second fixed frame 29b fixed to the inside wall of the main body 29. The second fixed frame 29b is arranged at the end of the camera attachment 19b of the main body 29.

The second zoom lens 25 is placed separable and opposite each other between the first and second fixed frames 29a and 29b. The second zoom lens 25 is fixed to the movable frame 26. On the outer circumference of the movable frame 26, the internal end of a guide pin 27 projected outward is fixed. The guide pin 27 is movably engaged along a cam groove 30 formed in the main body 29.

A ring-like guide groove 29c is formed on the outer circumference of the main body 29. In the guide groove 29c, the zoom dial 6 is fit rotatable around the axis O1. On the inner circumference of the zoom dial 6, an engagement groove 28 is formed extending parallel to the axis O1. The engagement groove 28 is engaged with the outer end of the guide pin 27. Thus, when the zoom dial 6 is rotated around the axis O1, the guide pin 27 moves along the cam groove 30 of the main body 29, and at the same time the guide pin 27 moves parallel to the axis O1 along the engagement groove 28. In this time, the second zoom lens 25 moves toward the axis O1 together with the guide pin 27 through the movable frame 26. As a result, the relative position of the first and second zoom lenses 24 and 25 is changed in the direction of axis O1, and the observing magnification is changed. Thus, a zoom optics with a variable magnification is configured.

The TV camera 7 is fixed removably to the camera attachment 19b of the main body 29. The TV camera 7 picks up the observation image of the endoscope 1 formed by the image-forming lens 31.

The thick part 1b of the endoscope 1 is provided with a plurality of fixing pins 11, for example, four substantially cylindrical pins, which constitute the attachment. These fixing pins 11 are arrange two each on both sides of the insertion axis O1 of the endoscope 1.

In FIG. 1, a reference numeral 12 denotes an endoscope holder. The endoscope holder 12 has a base 15 put movably on the floor, and a multi-joint arm unit 14. The base 15 has a plurality of casters 16 movable on the floor, and at least two stoppers 17. The casters 16 are arranged with a predetermined interval at the edge of the lower side of the base 15.

The stopper 17 has an operation lever 17a, a locking foot 17b, and a not-shown jack-up mechanism. The operation lever 17a is supported rotatable from the lock position to the unlock position. The jack-up mechanism contains a conversion mechanism which converts the rotation of the control lever 17a to a vertical movement by a well-known cam mechanism or the like. When the operation lever 17a of the stopper 17 is held at the unlock position, the locking foot 17b stands by at the ready position separated from the floor. In this state, the base 15 is held movable against the floor. When the operation lever 17a is rotated to the lock position, the locking foot 17b is brought in contact with the floor by the jack-up mechanism. In this state, the base 15 is fixed unmovable against the floor.

A pole 15a is set up on the upper surface of the base 15. The upper end of the pole 15a is connected with the base end of the arm unit 14. The arm unit 14 has a plurality of arms and joints put between the arms. The joint contains an electromagnetic clutch, for example. As the electromagnetic clutch of the joint turns on and off, the arms of the arm unit 14 are switched to a movable free state and an unmovable locked state.

The front end of the arm unit 14 is provided with an attachment 13 to fix removably a medical instrument.

Figure 3A:
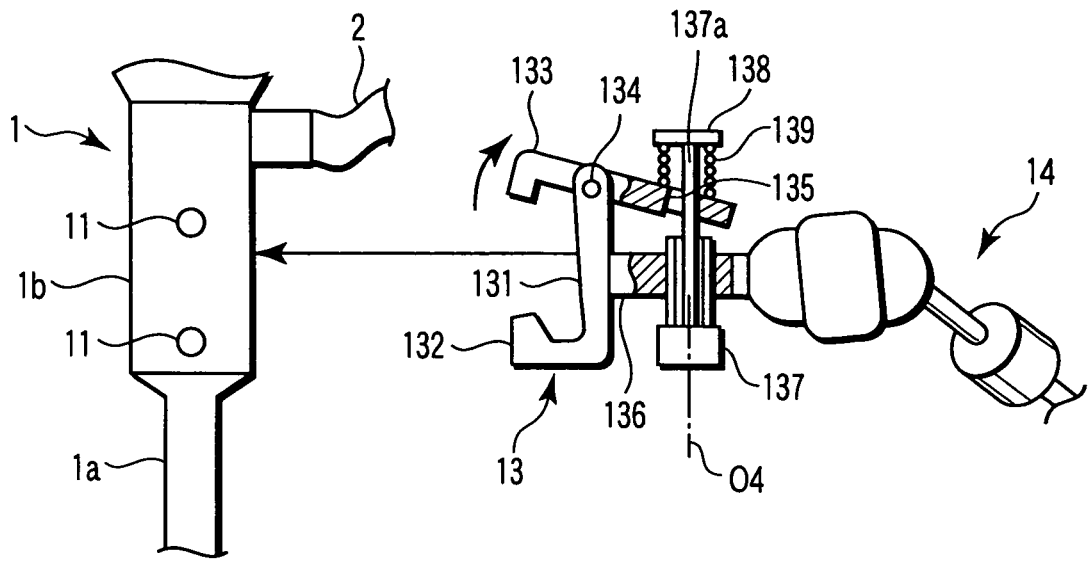
FIG. 3A is a view for explaining the opening operation of a movable claw when an endoscope holder of the endoscopic observation apparatus of the first embodiment is operated.
Figure 3B:
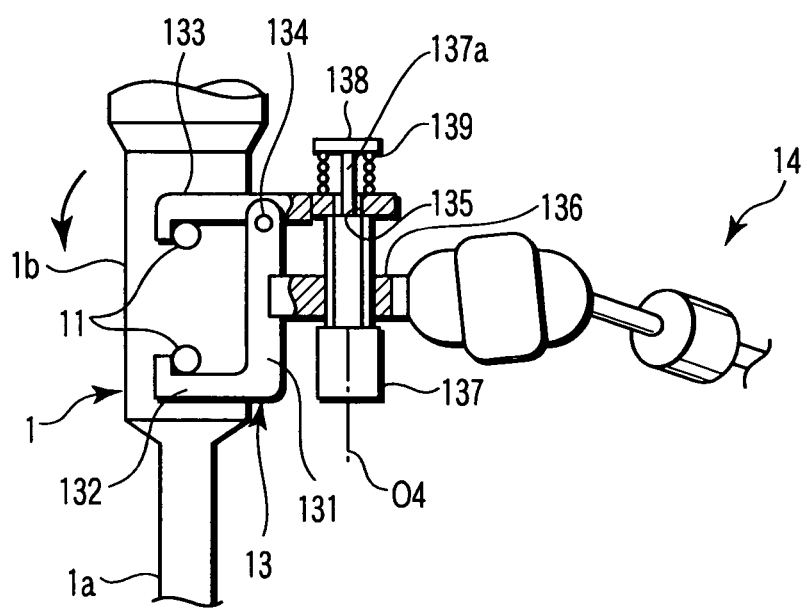
FIG. 3B is a view for explaining the closing operation of a movable claw when an endoscope holder of the endoscopic observation apparatus of the first embodiment is operated.

FIGS. 3A and 3B show the schematic configuration of the attachment 13 of the arm unit 14 of the endoscope holder 12 of this embodiment. In the main body 131 of the attachment 13, a pair of substantially L-shaped claws 132 is provided upward at the lower end of the front side in FIG. 1. These claws 132 are arranged with a predetermined interval in the horizontal direction of the main body 131 in FIG. 1, that is, an interval of the degree to be arranged on both sides of the thick part 1b of the endoscope 1. These claws 132 lock the two pins arranged in the lower side of the thick part 1b in FIG. 3A out of the four fixing pins 11 of the endoscope 1.

Further, at the upper end of the main body 131, a pair of substantially L-shaped movable claws 133 is provided downward against and substantially parallel to the claws 132. The middle parts of the movable claws 133 are supported rotatable by the main body 131 through a shaft 134. The base ends of the movable claws 133 are made as one body. The one body part of the movable claws 133 has an insertion hole 35.

In the rear side of the main body 131, a projection 136 connected to the arm unit 14 is provided. An attach-detach knob 137 is screwed to the projection 136 movably toward the axis O4 almost parallel to the axis O1. At the tip of the attach-detach knob 137, an extension part 137a inserted into the insertion hole 135 of the movable claw 133 and extended upward is formed. At the tip of the extension part 137a, a flange 138 for preventing omission is provided. A spring member 139 is attached between the flange 138 and the edge of the insertion hole 135 at the base end of the movable claw 133.

Thus, the movable claw 133 rotates around the shaft 134 according to the screwing amount of the attach-detach knob 137. In this time, as the movable claw 133 rotates clockwise around the shaft 134, the movable claw 133 separates from the claw 132 and closes, as shown by the arrow in FIG. 3A. As the movable claw 133 rotates counterclockwise around the shaft 134, the movable claw 133 moves toward the claw 132 and closes, as shown by the arrow in FIG. 3B.

Next, the effects of the above-mentioned configuration will be explained. When performing an operation using the endoscopic observation apparatus of this embodiment, first an operator connects the TV camera 7 to the endoscope 1 through the adapter 4. Then, connect the light guide 2 to the endoscope 1. Then, connect the endoscope 1 to the light source unit 3 through the light guide 2, and connect the TV camera 7 to the monitor 10 through the control unit 9.

Then, attach the endoscope 1 to the attachment 13 of the endoscope holder 12. In this time, first operate the attach-detach knob 137 of the endoscope holder 12. Adjust the screwing amount of the attach-detach knob 137, and rotate the movable claw 133 clockwise by the energizing force of the member 139, as shown by the arrow in FIG. 3A, thereby setting the movable claw 133 and claw 132 to the open state with a space therebetween. In this state, lock the fixing pin 11 of the insertion side of the endoscope 1 by the claw 132.

Next, rotate the attach-detach knob 137 reverse to the screwing direction. Then, the movable claw 133 is rotated counterclockwise against the energizing force of the spring member 139, as shown by the arrow in FIG. 3B, whereby the tip of the movable claw 133 locks the fixing pin 11 of the base end side of the endoscope 1, as shown in FIG. 3B.

Then, the endoscope 1 is fixed and supported by the endoscope holder 12 with the fixing pin 11 held between the claw 132 and movable claw 133 of the attachment 13 of the endoscope holder 12.

In this state that the endoscope 1 is held by the endoscope holder 12, an operator or a unit operator moves the base 15 to a desired position on the floor, and rotate the stopper 17 there to fix it on the floor.

In this fixed state, an operator holds the adapter 4 or TV camera 7, and operates the operation switch to set the lock of the joint of the endoscope holder 12 to the free state. In this state, insert the insertion part 1a of the endoscope 1 into a desired part.

When an operator adjusts the focus of the operating part, rotate the focus dial 5 of the adapter 4 around the axis 5a. By this action, the focus lens 20 is moved toward the axis O1 through the gear 23 and rack 22, and the focus is adjusted.

When changing the observing magnification, rotate the zoom dial 6 around the insertion axis O1. Then, the second zoom lens 25 is moved with the movable frame 26 toward the axis O1 through the pin 27, interlocking with the rotation of the zoom dial 6, whereby the magnification is changed. After repeating each operation and setting the observing conditions to a desired state as described above, an operator observes the image of a desired operating part on the monitor 10.

If the endoscope holder 12 becomes unnecessary during operation, an operator loosens the attach-detach knob 137 in the reverse order to the fixing, and removes the endoscope 1 from the attachment 13. Then, perform endoscopic observation while holding the endoscope 1, adapter 4 and TV camera 7 by hand.

The above-mentioned configuration has the following effects. Namely, in the endoscopic observation apparatus of this embodiment, two fixing pins 11 are arranged on both sides of the thick part 1b of the endoscope 1, and these fixing pins 11 are held releasable between the claw 132 and movable claw 133 of the attachment 13 of the endoscope holder 12. With this structure, the configuration of the endoscope holder 12 can be simplified compared with the case where the attachment of the endoscope holder is arranged all over the circumference of the thick part 1b of the endoscope 1. Thus, the whole size of the attachment 13 of the endoscope holder 12 can be made compact. This makes observation of the periphery of the insertion part 1a of the endoscope 1 easy, facilitating an operation.

Further, when attaching the endoscope 1 to the attachment 13 of the endoscope holder 12, the fixing pin 11 of the thick part 1b of the endoscope 1 is held and fixed between the claw 132 and movable claw 133 of the attachment 13 of the arm unit 14. Thus, the endoscope 1 attached to the attachment 13 of the endoscope holder 12 can be securely fixed without being slipped. As a result, the unit can be operated simply and easily, improving ease of operation.

Further, in this embodiment, the rotating directions of the focus dial 5 and zoom dial 6 are arranged substantially orthogonal to the adapter 4. By this arrangement, when observing an image, the operations of the focus dial 5 and zoom dial 6 can be easily recognized by their rotating directions. Therefore, an image focus and observation magnification can be exactly adjusted.

Embodiment 2

FIG. 4 to FIG. 7B show a second embodiment of the present invention. In this embodiment, the configuration of the endoscopic observation apparatus of the first embodiment (FIG. 1 to FIG. 3B) is modified as follows. In FIG. 4 to FIG. 7B, the same reference numerals are given to the same parts as those in FIG. 1 to FIG. 3B, and detailed explanation will be omitted.

Figure 4:
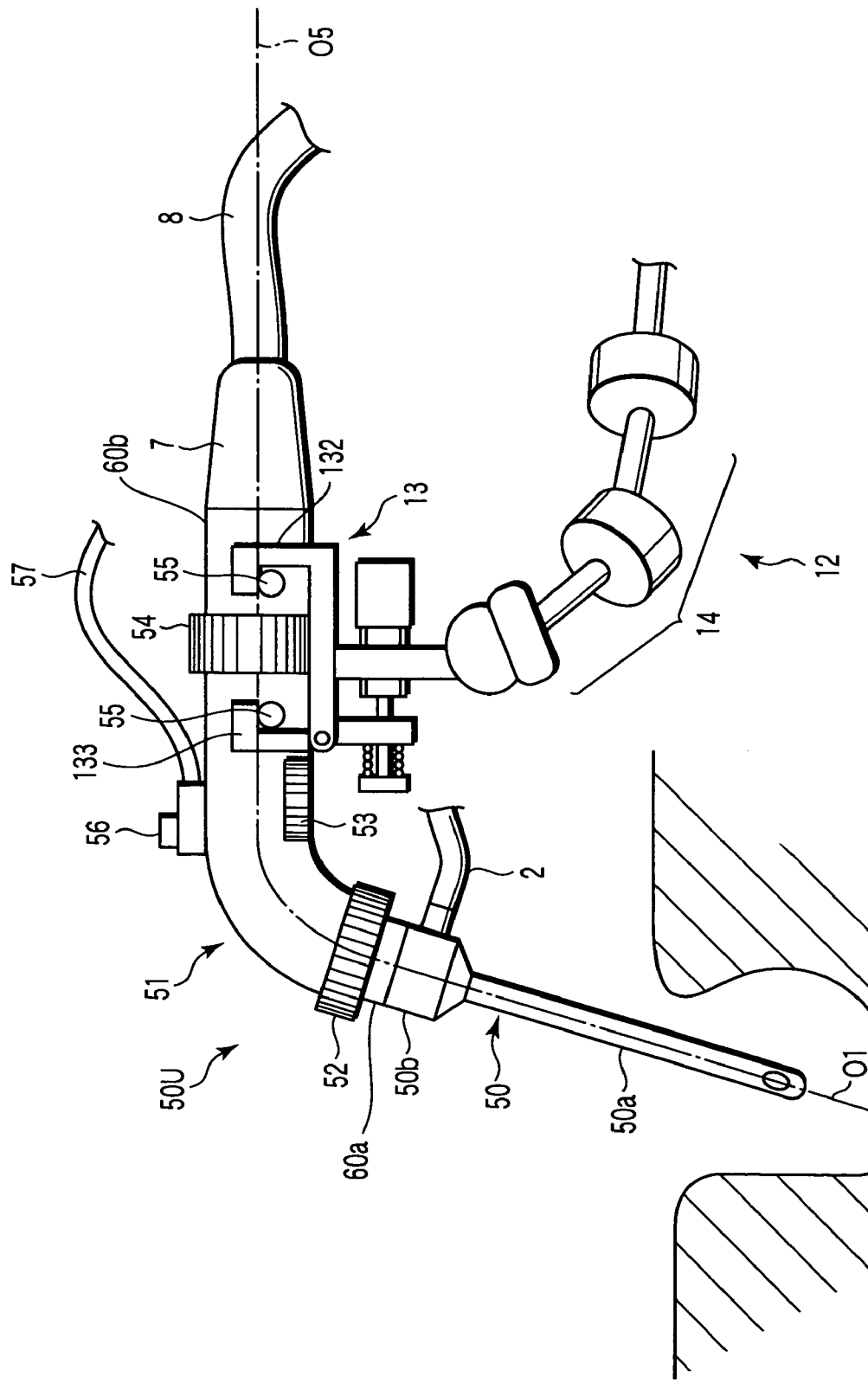
FIG. 4 is a schematic configuration of an essential part of an endoscopic observation apparatus according to a second embodiment of the present invention.

In FIG. 4 a reference numeral 50 denotes an endoscope. A thick part 50b of the endoscope 50 is connected at the base end of a slender insertion part 50a. The light guide 2 is connected removably to the thick part 50b.

An adaptor 51 is connected removably to the base end of the thick part 50b. The adapter 51 has a main body 60 bent substantially J-shaped. The middle part of the main body 60 is bent in the direction of about 90° against the insertion axis O1 of the endoscope 50 (in the direction of the axis O5).

The main body 60 has an endoscope connector 60a at one end, and a camera connector 60b at the other end. The endoscope 50 is connected optically removable to the endoscope connector 60a, as described later. The TV camera 7 is connected optically removable to the camera connector 60b, as described later.

The adapter 51 is provided with an image rotator dial 52, a focus dial 53, and a zoom dial 54. The image rotator dial 52 is supported rotatable around the insertion axis O1 of the endoscope 50. The focus dial 53 is supported rotatable around the axis of rotation vertical to the axis O5 and substantially parallel to the axis O1. The zoom dial 54 is supported movable around the axis O5.

Further, the adapter 51 has a plurality of arm holding pins almost the same as the four fixing pins 11 in the first embodiment, for example, four fixing pins 55 are projected in the direction vertical to the axis O5. The four fixing pins 55 are arranged two each on both sides of the axis O5 of the adapter 51.

Further, the adapter 51 is provided removably with a switch 56. The switch 56 is connected to a not-shown brake control means through a cable 57. The brake control means (not shown) locks and unlocks the joints of the arm unit 14 of the endoscope holder 12, reacting on the switching operation of the switch 56.

Figure 5:
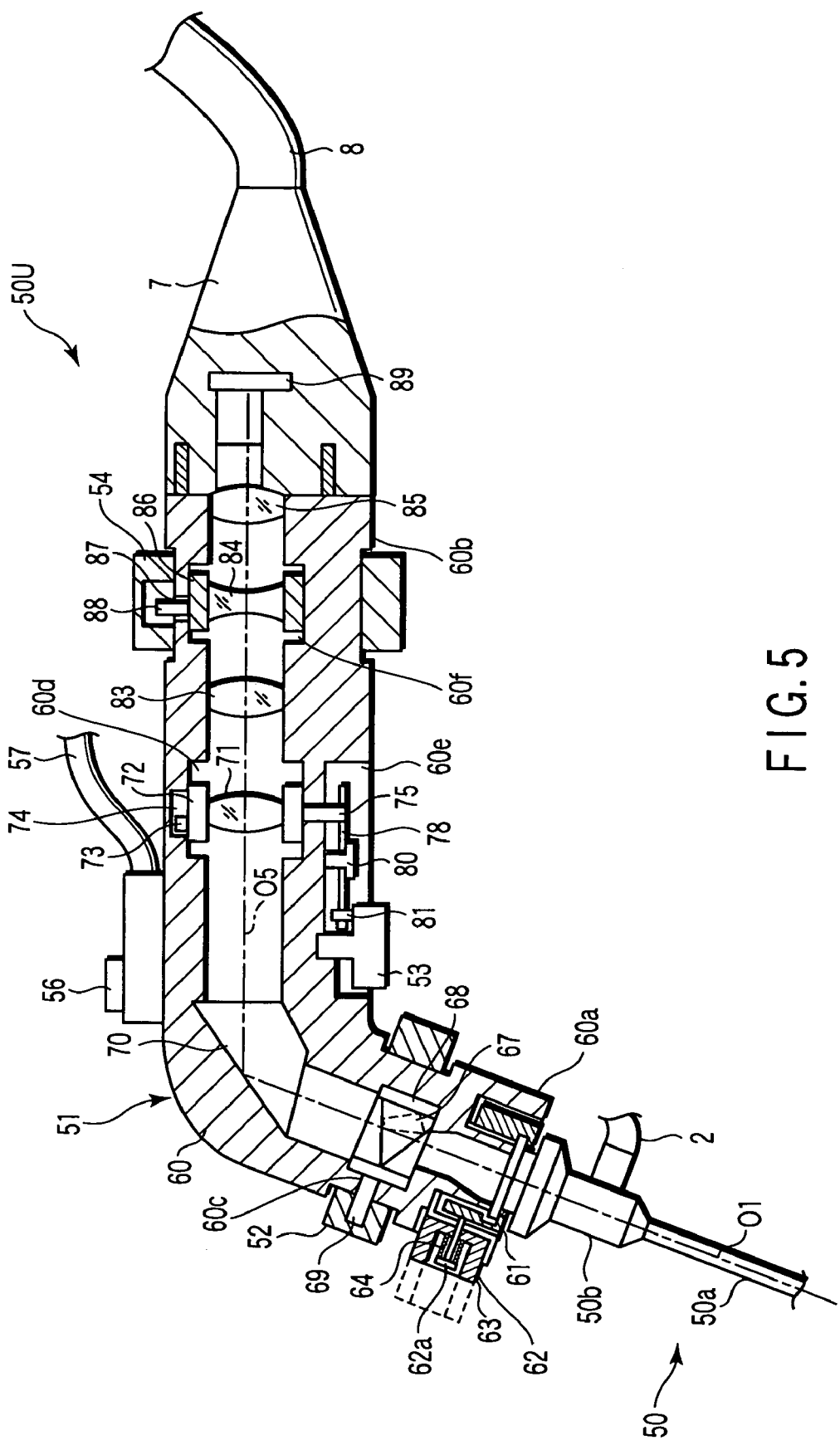
FIG. 5 is a side view, partially cross sectioned, of the internal structure of an adapter of the endoscopic observation apparatus of the second embodiment.

FIG. 5 shows the internal structure of the adapter 51. A fixing ring 61 is fit adjustably to the endoscope connector 60a of the adapter 51. The base end of the thick part 50b of the endoscope 50 is inserted removably into the fixing ring 61.

The fixing ring 61 has a projected fixing pin 62 on the outer circumference. The fixing pin 62 is inserted into a cylindrical fixing knob 63 with a bottom. A spring receiving flange 62a is formed at the tip of the fixing pin 62. A spring member 64 is attached between the bottom of the fixing knob 63 and the flange 62a of the fixing pin 62. Thus, the fixing knob 63 is fit slidable along the fixing pin 62 of the fixing ring 61.

Figure 6:
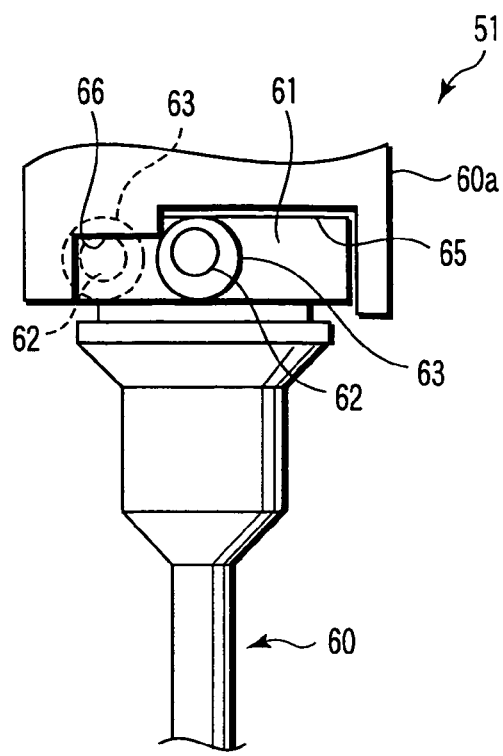
FIG. 6 is a side view for explaining the structure of an attachment of the endoscope of the second embodiment.

In the main body 60, a groove 65 is formed in the circumferential wall of the endoscope connector 60a, as shown in FIG. 6. The width of this first groove 65 is set larger than the outside diameter of the fixing knob 63. At one end of the first groove 65, a second groove 66 is formed in the state connecting with the first groove. The width of the second groove 66 is set smaller than the fixing knob 63 and larger than the outside diameter of the flange 62a of the fixing pin 62.

Inside the main body 60, a prism 70 constituting a refracting means is arranged at the bent position (the crossing point between the axes O1 and O5). The axis O1 coincides with the optical axis O1 of the endoscope 50. The axis O5 coincides with the optical axis O5 of the TV camera 7 (an image pickup element 89 described later).

A rotator prism 67 is arranged on the axis O1 at the location more close to the endoscope connector 60a than the prism 70. At the location more close to the camera connector 60b than the prism 70, a focus lens 71, a fixed zoom lens 83, a movable zoom lens 84 and an image-forming lens 85 are sequentially arranged on the axis O5.

The rotator prism 67 is held through a cylindrical holding member 68. The holding member 68 is held rotatable around the axis O1 with respect to the main body 60. A pin 69 is projected on the outer circumference of the holding member 68.

In the main body 60, a guide hole 60c to accept the pin 69 is made at the rotator dial 52 fitting position. The guide hole 60c is formed by an elongate hole in the circumferential direction of the main body 60. The pin 69 is inserted into the guide hole 60c, and the rotator dial 52 is fit to the tip of the pin. Thus, the holding member 68 is rotated around the axis O1 together with the rotator prism 67 through the pin 69, interlocking with the rotation of the rotator dial 52 around the axis O1. The rotation angle of an observation image is adjusted by the rotational movement of the rotator prism 67 at this time.

Further, in the main body 60, the prism 70 is arranged in the output side of the rotator prism 67. The prism 70 refracts an incident light toward the optical axis O5 that is placed at about 90° against the axis O1, and outputs the light to the focus lens 71.

The focus lens 71 is held by a cylindrical holder 72. On the inner circumference of the main body 60, a guide groove 60d is formed to support the holder 72 movable in the direction of the optical axis O5. Thus, the focus lens 71 is supported movable toward the optical axis O5 with respect to the main body 60 through the holder 72.

A guide pin 73 and a movable pin 75 are projected on the outer circumference of the holder 72. The tip of the guide pin 73 is fit movably in the cam groove 74 on the inner circumference of the main body 60. The cam groove 74 is formed at the inside bottom of the guide groove 60d.

The tip of the movable pin 75 is projected on the side of the focus dial 53, as shown in FIG. 5. On the outer circumference of the main body 60, a link mechanism housing cavity 60e is formed on the side of the focus dial 53. The tip of the movable pin 75 projects into the link mechanism housing cavity 60e.

The link mechanism housing cavity 60e contains a link plate 78. The substantially middle part of the link plate 78 is supported rotatable by the main unit 60 through a link shaft 80. The link shaft 80 has an axis O6 substantially orthogonal to the axis O5.

Figure 7A:
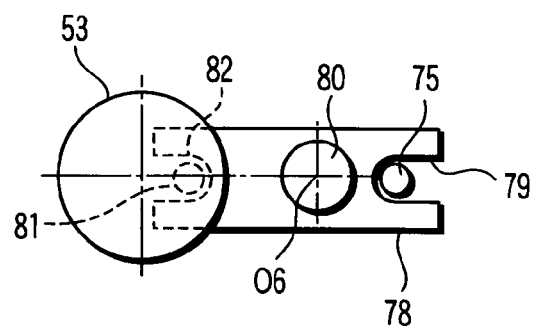
FIG. 7A is a view for explaining the state that a link plate is held at the initial position when the focus dial of the adapter of the second embodiment is operated.
Figure 7B:
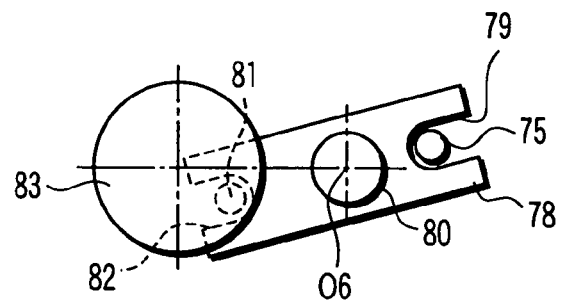
FIG. 7B is a view for explaining the state that the link plate is rotated when the focus dial of the adapter of the second embodiment is operated.

The link plate 78 has a groove 79 at one end, and a groove 82 at the other end, as shown in FIG. 7A. The tip of the movable pin 75 is inserted movably into the groove 79 at one end of the link plate 78. A pin 81 provided in the focus dial 53 is inserted into the groove 82 at the other side of the link plate 78.

When the focus of the focus lens 71 is adjusted, the focus dial 53 is rotated. In this time, the link plate 78 rotates around the link shaft 80 corresponding to the rotating direction of the focus dial 53. The holder 72 rotates together with the focus lens 71 through the movable pin 75, interlocking with the rotational movement of the link plate 78. The holder 72 moves toward the axis O5 together with the focus lens 71 by the actions of the guide pin 73 and cam groove 74, interlocking with the rotational movement of the holder 72. By this operation, the focus of the focus lens 71 is adjusted.

The emergent light from the focus lens 71 is guided to the TV camera 7 through the fixed zoom lens 83, movable zoom lens 84 and image-forming lens 85. The movable zoom lens 84 is held by a ring-like holder 86. A guide groove 60f to support the holder 86 movably in the direction of the optical axis O5 is formed on the inner circumference of the main body 60. Thus, the movable zoom lens 84 is supported movably in the direction of the axis O5 through the holder 86.

A pin 88 is projected on the outer circumference of the holder 86. The pin 88 is inserted into a cam groove 87 formed in the main body 60, and projected to the outside of the main body 60. The tip of the pin 88 is engaged with the inner circumference of the zoom dial 54. Thus, when zoom dial 54 is rotated around the axis O5, the pin 88 is guided by the cam groove 87, and the holder 86 is moved parallel to the axis O5 just like one unit with the movable zoom lens 84. In this time, the magnification of an observation image is changed by the movement of the movable zoom lens 84.

The TV camera 7 is fit removably to the other end of the main body 60. The TV camera 7 contains an image pickup element 89. The luminous flux guided through the image-forming lens 85 is applied to the image-forming element 89, and an image is picked up.

Next, the effects of the above-mentioned embodiment will be explained. When using the endoscopic observation apparatus of this embodiment, first an operator connects the adapter 51 to the base end of the thick part 50b of the endoscope 50. When making the connection, pull the fixing knob 63 of the endoscope connector 60a of the adapter 51. In this time, while raising the fixing knob 63 outward against the spring member 64, rotate the fixing ring 61, as shown by the dotted line in FIG. 5. And, move the fixing knob 63 to the second groove 66, as shown by the dotted line in FIG. 6.

In this state, insert one end of the thick part 50b of the endoscope 50 into the fixing ring 61. Next, rotate the fixing ring 61 in the reverse direction. Then, the fixing knob 63 comes out of the second groove 66, and falls into the first groove 65. By rotating the fixing ring 61 furthermore in this state, the thick part 50b of the endoscope 50 is fixed to the fixing ring 61. Next, connect the TV camera 7 to the camera connector 60b of the main body 60. Then, an endoscopic observation unit (observation means) 50U is assembled completely, in which the endoscope 50 is connected to the TV camera 7 through the adapter 51.

Then, fix the endoscopic observation unit 50U to the fixing unit 13 of the arm unit 14 of the endoscope holder 12. When fixing the endoscopic observation unit 50U, grip the fixing pins 55 of the main body 60 of the adapter 51 releasably between the claw 132 and movable claw 133 of the fixing unit 13, as in the first embodiment. Then, the endoscopic observation unit 50U is fit in the endoscope holder 12.

After fitting the endoscopic observation unit 50U, an operator inserts the endoscope 50 into a desired operating part by pressing the switch 56. Then, operate the endoscopic observation unit 50U as follows. For example, when adjusting the direction of an observation image, rotate the rotator dial 52 around the axis O1. In this time, the holding member 68 and rotator prism 67 are rotated around the axis O1, interlocking with the rotation of the rotator dial 52. Then, an observation image displayed on the monitor 10 is rotated, and the direction of the image is adjusted.

When adjusting the focus of an observation image to a desired position, rotate the focus dial 53. When the focus dial 53 is rotated, the holder 72 is rotated through the pin 81, link plate 78 and movable pin 75 of the focus dial 53. Interlocking with the rotation of the holder 72, the holder 72 and focus lens 71 are moved in the direction of the axis O5 by the effect of the pin 73 and cam groove 74 of the holder 72, and the focus is adjusted.

When adjusting the magnification of an observation image, rotate the zoom dial 54 around the axis O5. In this time, the holder 86 and movable zoom lens 84 are rotated through the pin 88 by the rotation of the dial 54. In this time, the pin 88 is guided by the cam groove 87, and moved in the direction of the axis O5 simultaneously with the rotation. Then, the movable zoom lens 84 is moved in the direction of the axis O5, and the magnification is changed.

When replacing the present endoscope 50 by another one, for example, an endoscope having different diameter and direction of observation, use the following procedure. First, remove the endoscope 50 from the adapter 51. In this time, hold the fixing knob 63 while gripping the endoscope 50 by hand, and rotate the fixing ring 61 in the reverse direction to fixing. Then, the fixing knob 63 comes in contact with the second groove 66 narrower than the first groove 65.

In this state, rotate the fixing ring 61 furthermore while pulling the fixing knob 63 by the force larger than the repulsive force of the spring member 64, thereby moving the fixing ring 61 into the second groove 66, and removing the endoscope 50 from the adapter 51.

Thereafter, attach another endoscope 50 with a different observing direction and different insertion part shape to the adapter 51, and perform endoscopic observation.

The above-mentioned configuration has the following effects. Namely, in the endoscopic observation apparatus of this embodiment, the fixing pins 55 are provided in the adapter 51, and the fixing pins 55 are held removable between the claw 132 and movable claw 133 of the fixing unit 13 of the endoscope holder 12. With this structure, the fixing unit 13 of the arm unit 14 does not exist near the endoscope 50 in the state that the endoscopic observation unit 50U is attached to the endoscope holder 12, and the operating space is not obstructed by the fixing unit 13 and endoscope holder 12. This facilitates an operation.

Further, in this embodiment, the a refracting prism 70 is provided in the adapter 51, the axis O5 is arranged substantially orthogonal to the insertion axis O1 of the endoscope 50, and the focus lens 71, fixed zoom lens 83, movable zoom lens 84 and TV camera 7 are arranged on the axis O5. With this structure, the portions of the endoscopic observation unit 50U projecting toward the axis O1 can be minimized. As a result, when using the endoscopic observation unit 50U together with a microscope for an operation, for example, interference between the microscope and endoscopic observation unit 50U is prevented, and an operation becomes still easier.

Further, the rotator dial 52 is rotated around the axis O1, the focus dial 53 is rotated around the rotation axis substantially parallel to the axis O1, and the zoom dial 54 is rotated around the axis O5. Thus, the rotator dial 52, focus dial 53 and zoom dial 54 can be easily distinguished by rotating the dials around their respective rotation axes. As a result, an operation can be performed efficiently without confusing the dials 52, 53 and 54.

Further, the fixing knob 63 for fixing an endoscope is provided in the endoscope connector 60a of the adapter 51, and the first and second grooves 65 and 66 are formed in the main body 60 corresponding to the fixing knob 63. When the endoscope 50 is attached and detached to/from the endoscope connector 60a of the adapter, the fixing knob 63 is moved along the first and second grooves 65 and 66. Therefore, the endoscope 50 is prevented from coming off even if the fixing knob 63 is incorrectly operated.

Embodiment 3

Figure 9:
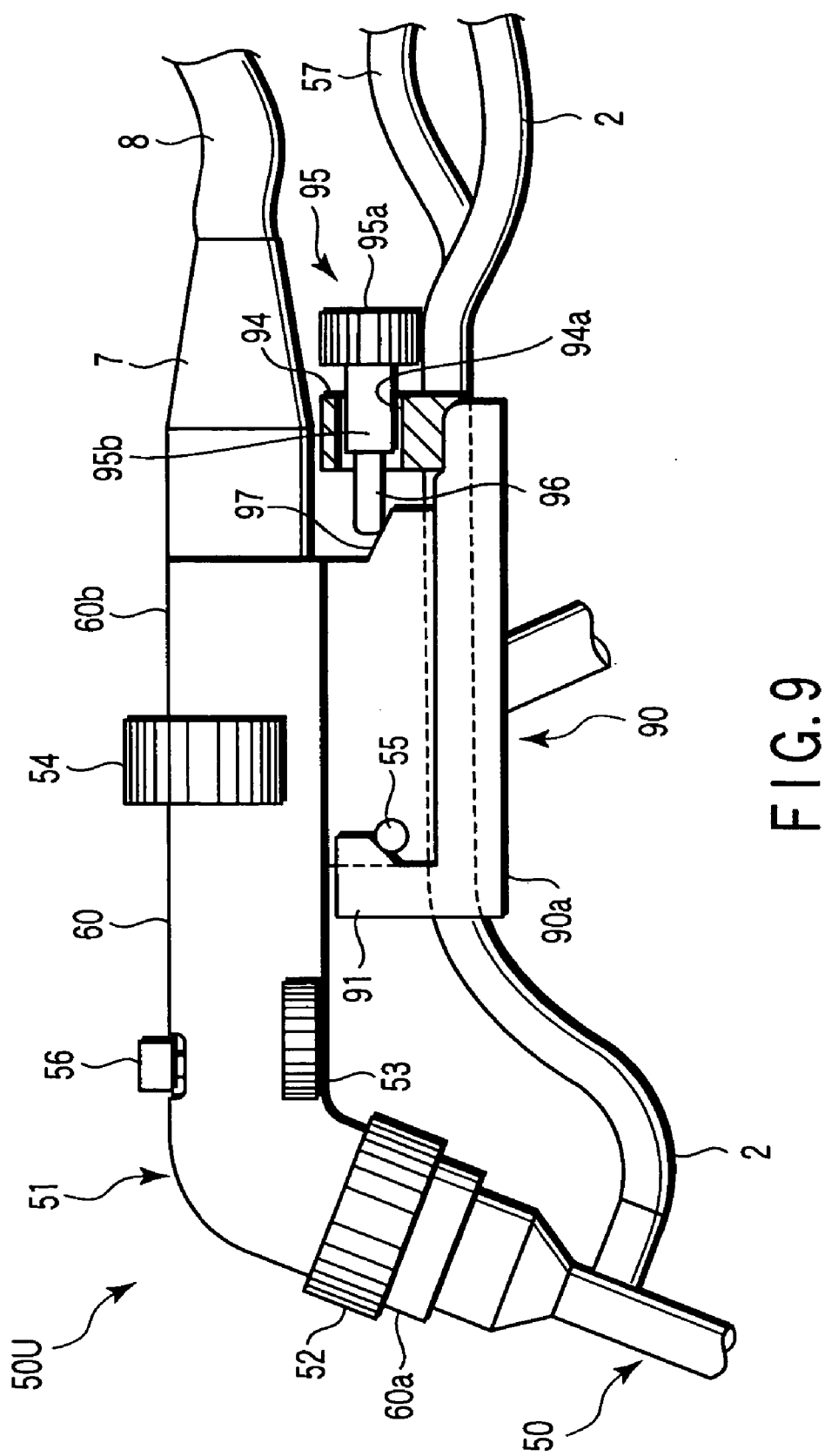
FIG. 9 is a side view showing the state of fixing an arm unit of the endoscopic observation apparatus according to the third embodiment of the present invention.

FIG. 8 and FIG. 9 show a third embodiment of the present invention. In this embodiment, the configuration of the endoscopic observation apparatus of the second embodiment (FIG. 4 to FIG. 7B) is modified as follows. In FIG. 8 and FIG. 9, the same reference numerals are given to the same parts as those in FIG. 4 to FIG. 7B, and detailed explanation will be omitted.

Namely, in this embodiment, a fixing unit 90 with different structure from the fixing unit 13 of the second embodiment is provided at the front end of the arm unit 14 of the endoscope holder 12. In the fixing unit 90, a base plate 90a to hold the adapter 51 of the endoscopic observation unit 50U is provided. On the upper surface of the base plate 90a, two (first and second) cavities 92 and 93 are formed substantially parallel to each other. One or first cavity 92 can contain the cable 57 of the switch 56 of the adapter 51. The other or second cavity 93 can contain the light guide 2 removable from the endoscope 50.

A pair of claws 91 is provided at the front end of the base plate 90a. The claws 91 can selectively lock the two fixing pins 55 on the left and right of the main body 60 of the adapter 51.

Further, at the rear end of the base plate 90a, a block-like rear part fixing piece 94 is projected at almost the middle of the width of the base plate. A screw hole 94a is made in the rear part fixing piece 94. The screw hole 94a is extended along the longitudinal direction of the fixing unit 90. A fixing screw member 95 is inserted into the screw hole 94a. The fixing screw member 95 is provided with a fixing knob 95a and a male screw 95b. By the rotation of the fixing knob 95a, the male screw 95b is inserted in the longitudinal direction along the screw hole 94a. A press part 96 is provided at the tip of the male screw 95b.

In the main body 60 of the adapter 51, a sloped stopper 97 is provided at the rear end of the camera connector 60b, as shown in FIG. 9. The press part 96 of the fixing screw member 95 is butt against the stopper 97. When fixing the endoscopic observation unit 50U to the fixing unit 90 of the endoscope holder 12, engage a pair of claws 91 of the fixing unit 90 with the pins 55 of the main body 60 beforehand. In this state, rotate the fixing knob 95a of the fixing screw member 95. By this operation, the male screw 95b is inserted forward along the screw hole 94a, and the press part 96 of the male screw 95b is butted against and stopped by the stopper 97 of the adapter 51. Then, the adapter 51 is fit removably to the fixing unit 90 of the endoscope holder 12.

Next, the effects of this embodiment with the above-mentioned structure will be explained. When using the endoscopic observation apparatus of this embodiment, first connect the endoscope 50 to the TV camera 7, whereby the endoscopic observation unit 50U is assembled as in the second embodiment. In this state, connect the light guide 2 to the endoscope 50.

Thereafter, loosen the fixing knob 95a of the fixing unit 90. In this state, hold the adapter 51 by hand, and place the light guide 2 and cable 57 in the first and second cavities 92 and 93 of the fixing unit 90. In this state, engage the claws 91 of the fixing unit 90 with the fixing pins 55 of the adapter 51.

Then, insert the fixing knob 95a into the rear part fixing piece 94, and bring the press part 96 of the male screw 95b into press contact with the stopper 97 of the adapter 51. Then, the adapter 51 is fixed to the fixing unit 90, and the endoscopic observation unit 50U is fixed to the fixing unit 90 of the endoscope holder 12.

In this fixed state, endoscopic observation is performed as in the second embodiment. In this time, the middle parts of the cable 57 and light guide 2 are placed in the first and second cavities 92 and 93 of the fixing unit 90, and the positions of other parts of the cable 57 and light guide 2 are controlled by the main body 60 of the adapter 51.

When the endoscope holder 12 is unnecessary, an operator can remove the endoscopic observation unit 50U from the endoscope holder 12 in the sequence reverse to the fixing. Namely, loosen the fixing knob 95a of the fixing unit 90, and release the engagement of the fixing pins 55 of the adapter 51 with the claws 91 of the fixing unit 90. In this state, remove the adapter 51 from the fixing unit 90, and use the endoscope 50 directly.

The above-mentioned configuration has the following effects. Namely, in this embodiment, a pair of claws 91 is provided at the front end of the base plate 90a of the fixing unit 90 of the endoscope holder 12, and the rear part fixing piece 94 and fixing screw member 95 are provided at the rear end of the base plate 90a. By screwing the fixing knob 95a of the fixing screw member 95 in the stat that the claws 91 are engaged with the pins 55 of the main body 60 of the adapter 51, the press part 96 is touched and pressed to the stopper 97 of the main body 60. By this operation, the adapter 51 can be supported by the fixing unit 90 at the three points of a pair of claws 91 and the press part 96 of the fixing screw member 95.

Therefore, as the adapter 51 can be stably fixed to the fixing unit 90 at three support points, the adapter can be fixed securely to the fixing unit 90 without a so-called "rattle".

Further, the first and second cavities 92 and 93 are formed in the base plate 90a of the fixing unit 90, and a part of the cable 57 and light guide 2 is placed and fixed in the first and second cavities 92 and 93. This prevents movement of the cable 57 and light guide 2 during operation, facilitating an operation. Further, when moving and operating the endoscope 50, it is unnecessary to take care of undesired movement of the cable 57 and light guide 2, and ease of operation is improved.

Embodiment 4

Figure 10:
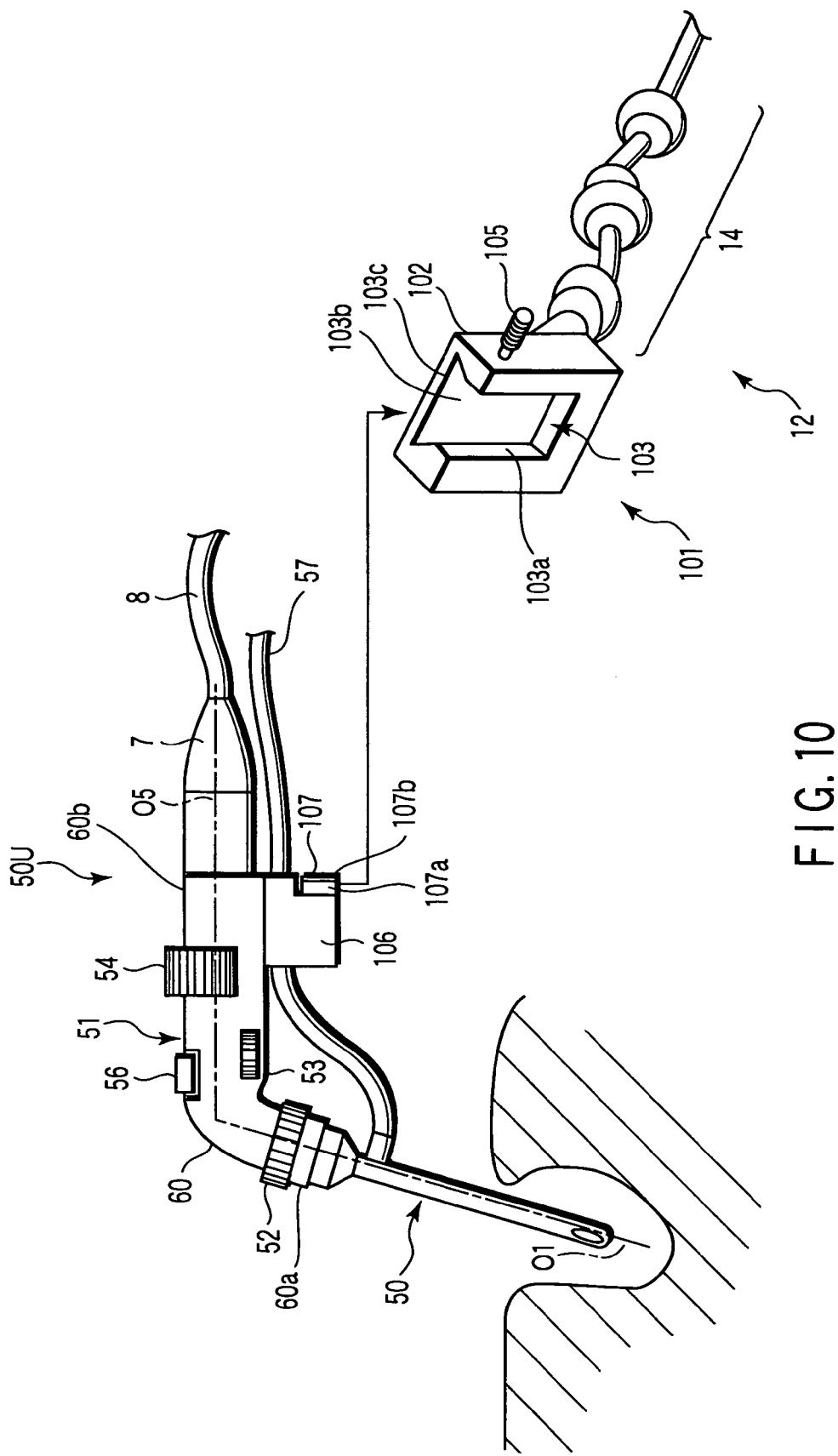
FIG. 10 is a schematic configuration of an essential part of an endoscopic observation apparatus according to a fourth embodiment of the present invention.
Figure 11:
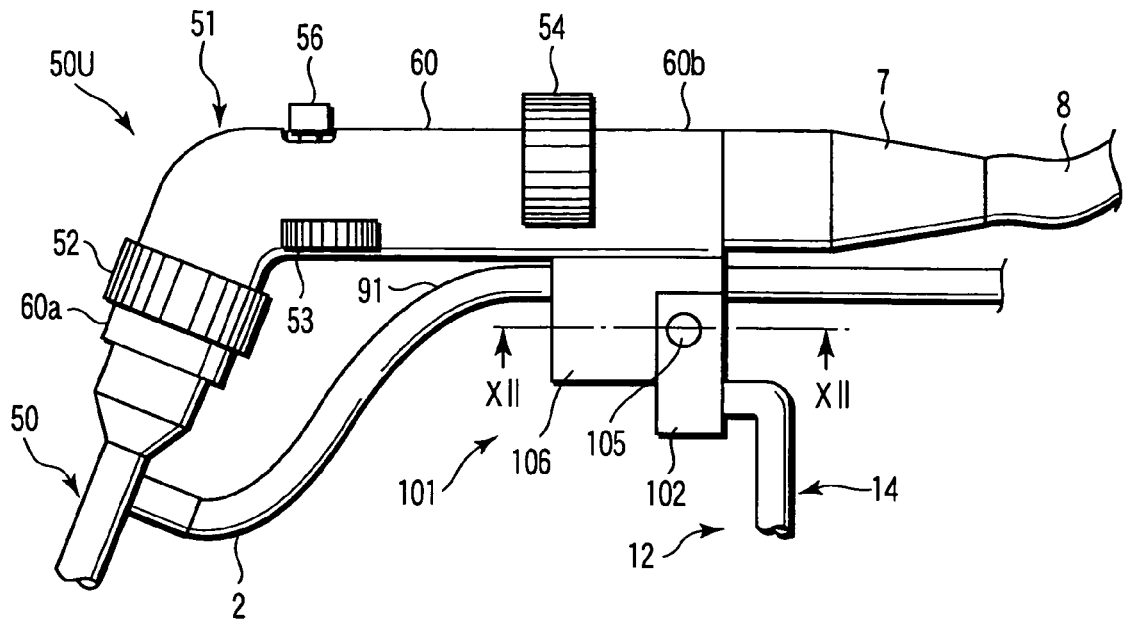
FIG. 11 a side view showing the state of fixing an arm unit of the endoscopic observation apparatus according to the fourth embodiment of the present invention.
Figure 12:
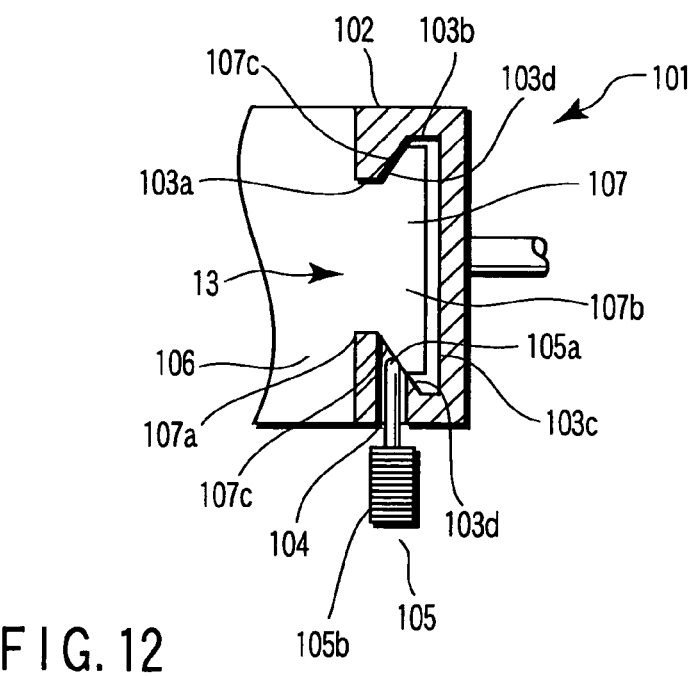
FIG. 12 is a sectional view taken along a line XII-XII of FIG. 11.

FIG. 10 to FIG. 12 shows a fourth embodiment of the present invention. In this embodiment, the structure of fixing the adapter 51 of the endoscopic observation unit 50U of the second embodiment (FIG. 4 to FIG. 7B) to the endoscope holder 12 is modified as follows.

Namely, in this embodiment, a fixing unit 101 with the structure different from the fixing unit 13 of the second embodiment is provided at the front end of the arm unit 14 of the endoscope holder 12. The fixing unit 101 is provided with a base block 102 to hold the adapter 51 of the endoscopic observation unit 50U. A dovetail groove 103 is formed in this base block 102.

FIG. 12 shows the cross sectional shape of the base block 102. The dovetail groove 103 has a narrow opening 103a and a wide opening 103b. The narrow opening 103a is arranged on the front side of the base block 102. The wide opening 103b is arranged in the rear of the narrow opening 103a (in the direction of the groove bottom 103c: on the right in FIG. 12). In the wide opening 103b, a pair of left and right slopes 103d is formed between the groove bottom 103c and the rear end of the narrow opening 103a. These slopes 103d are inclined like a V-shape in the state that the groove width gradually becomes narrow toward the front side.

A screw hole 104 is made on the side of the base block 102. The opening at the inside end side of the screw hole 104 is arranged on one of the slopes 103d. A fixing screw 105 as a stopper is inserted externally into the screw hole 104. The fixing screw 105 is provided with a male screw 105a to be inserted into the screw hole 104 and a screw head 105b connected to the outside end of the male screw 105a.

Further, in the adapter 51 of the endoscopic observation unit 50U, a block-like connection member 106 is provided at the end of the camera connector 60b. The connection member 106 is arranged on the side of the endoscope connector 60a of the main body 60 of the adapter 51. A dovetail joint (fixed part) 107 is projected in the rear side of the connection member 106. The dovetail joint 107 is extended in the direction substantially identical to the insertion direction (the direction of the axis O1) of the insertion part 50a of the endoscope 50.

The dovetail joint 107 is formed by the projection shaped corresponding to the dovetail groove 103 of the endoscope holder 12. Namely, the dovetail joint 107 has a narrow part 107a and a wide part 107b. The narrow part 107a is arranged in the side joined to the connection member 106, and shaped corresponding to the narrow opening 103a. The wide part 107b is arranged at the front end of the narrow part 107a, and shaped corresponding to the wide opening 103b of the dovetail groove 103. Further, on both sides of the wide part 107b, a V-shaped slope 107c is formed expanding gradually toward the front end.

Next, the effects of the above-mentioned configuration will be explained. In this embodiment, when fixing the endoscopic observation unit 50U to the fixing unit 101 of the arm unit 14 of the endoscope holder 12, insert the dovetail joint 107 of the adapter 51 of the endoscopic observation unit 50U into the dovetail groove 103 of the fixing unit 101. In this time, the narrow part 107a of the dovetail joint 107 of the adapter 51 is inserted into the narrow opening 103a, and the wide part 107b is inserted into the wide opening 103b of the dovetail groove 103. The dovetail joint 107 of the adapter 51 is inserted along the dovetail groove 103 in the direction substantially identical to the insertion direction (the direction of the axis O1) of the insertion part 50a of the endoscope 50.

When the dovetail joint 107 is inserted up to the backend position during insertion of the dovetail joint 107, the dovetail joint 107 comes in contact with the backend of the dovetail groove 103 and the insertion is stopped. By inserting the fixing screw 105 in this state, the fixing screw 105 comes in contact with the dovetail joint 107 as shown in FIG. 12. In this time, the tip of the male screw 105a is pressed to contact with the slope 107c of the wide part 107b of the dovetail joint 107. This prevents the dovetail joint 107 of the adapter 51 inserted into the dovetail groove 103 of the endoscope holder 12 from coming out of the dovetail groove 103.

When removing the endoscopic observation unit 50U from the fixing unit 101 of the arm unit 14 of the endoscope holder 12, loosen the fixing screw 105 and move the unit 50U in the direction of removing the dovetail joint 107 of the adapter 51 from the dovetail groove 103 of the endoscope holder 12. In this time, dovetail joint 107 of the adapter 51 is moved along the dovetail groove 103 in the reverse direction to the insertion direction (the direction of the axis O1) of the insertion part 50a of the endoscope 50. Then, the endoscopic observation unit 50U is removed from the fixing unit 101 of the arm unit 14 of the endoscope holder 12.

The above-mentioned configuration has the following effects. Namely, in this embodiment, the dovetail groove 103 is formed in the fixing unit 101 of the endoscope holder 12, and the dovetail joint 107 is projected from the adapter 51 of the endoscopic observation unit 50U. With this structure, when attaching and detaching the endoscopic observation unit 50U to/from the fixing unit 101 of the arm unit 14 of the endoscope holder 12, the unit 50U can be attached and detached by moving the adapter 51 of the endoscopic observation unit 50U in the direction substantially identical to the insertion direction (the direction of the axis O1) of the insertion part 50a of the endoscope 50. Therefore, the position of the endoscope holder 12 supporting the endoscope 50 is not changed when attaching and detaching the endoscopic observation unit 50U, the brake of each joint of the arm unit 14 of the endoscope holder 12 is held locked.

As a result, the endoscope 50 can be removed from the endoscope holder 12 more easily compared with the case when removing after releasing the endoscope holder 12 and separating the endoscope 50 away from an operating part. Therefore, the endoscope 50 can be removed quickly during operation.

Further, if the dovetail joint 107 with the same structure as the dovetail joint 107 of the adapter 51 of the endoscopic observation unit 50U is provided in other treatment tools such as an ultrasonic probe and an endoscope with a different slant view angle, the ultrasonic probe and endoscope can be exactly located at the observation position of the present endoscope 50.

Embodiment 5

Figure 13:
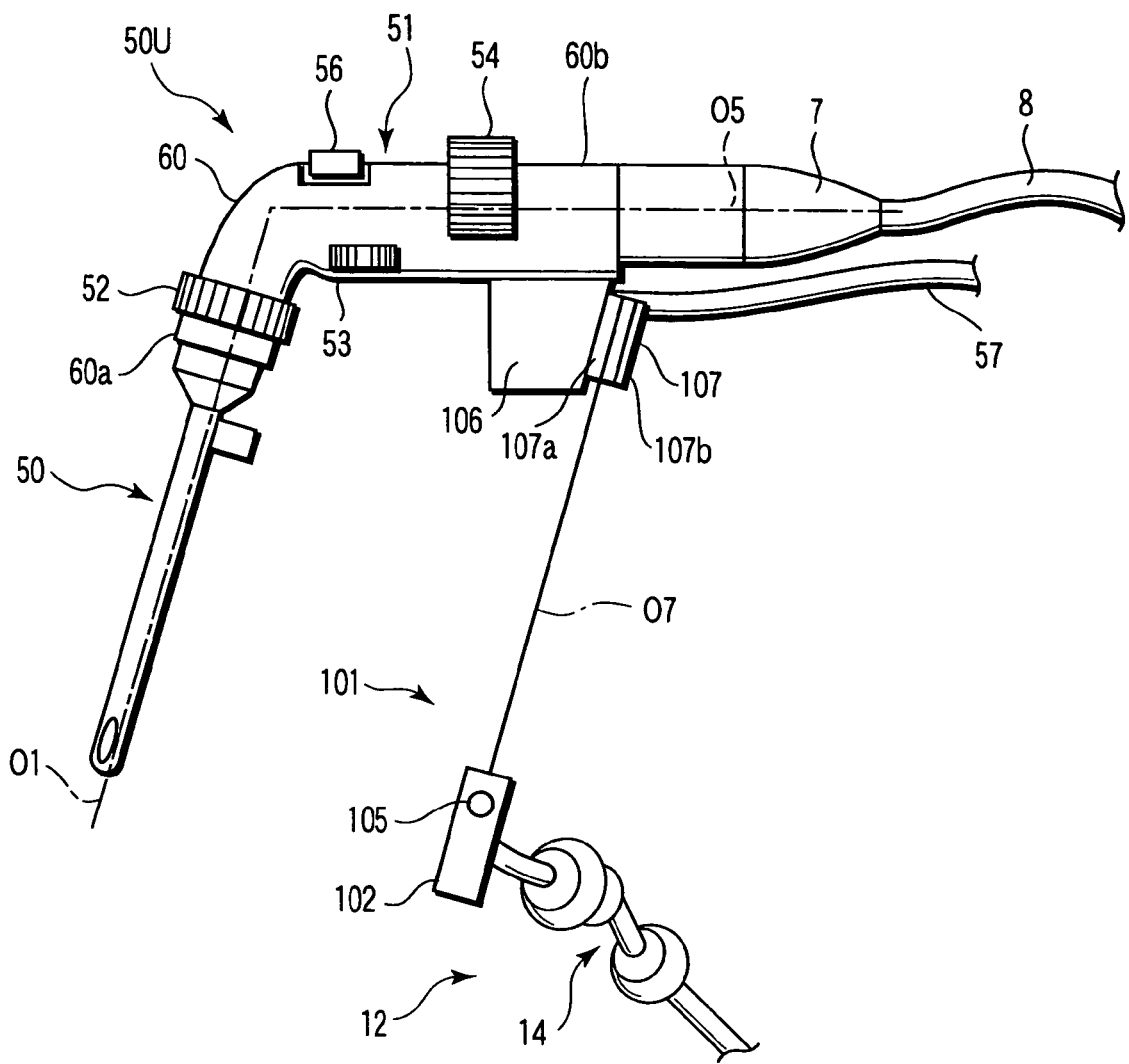
FIG. 13 is a schematic configuration of an essential part of an endoscopic observation apparatus according to a fifth embodiment of the present invention.

FIG. 13 shows a fifth embodiment of the present invention. In this embodiment, the relation between the dovetail groove 103 of the fixing unit 101 of the endoscope holder 12 and the dovetail joint 107 of the adapter 51 of the endoscopic observation unit 50U of the fourth embodiment (FIG. 10 to FIG. 12) is modified as follows.

Namely, in this embodiment, the extension direction O7 of the dovetail joint 107 of the adapter 51 is arranged parallel to the insertion direction (the direction of the axis O1) of the insertion part 50a of the endoscope 50 connected to the endoscope connector 60a.

In this case, when attaching and detaching the endoscopic observation unit 50U to/from the fixing unit 101 of the arm unit 14 of the endoscope holder 12, the unit 50U can be attached and detached by moving the adapter 51 of the unit 50U in the direction identical to the insertion direction (the direction of the axis O1) of the insertion part 50a of the endoscope 50. Therefore, the insertion part 50a of the endoscope 50 is prevented from shifting in the other directions than the insertion direction when attaching and detaching the endoscopic observation unit 50U. This makes it easer to replace a medical device to be held by the fixing unit 101 of the arm unit 14 of the endoscope holder 12 from the endoscope 50 to other treatment tools.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic observation apparatus comprising:
    an endoscopic observation unit comprising an endoscope which has an insertion part and an observation axis extending in an insertion direction of the insertion part, the insertion part having a distal end, a base end and an insertion axis, and insertable into a body cavity;
    an adapter which is fit removably to the base end of the endoscope;
    an image pickup camera which is fixed to the endoscope through the adapter, and picks up an image obtained by the endoscope through the adapter, the camera having an image pickup optical axis, wherein the endoscope, adapter and image pickup camera are combined;
    a plurality of fixed parts which are arranged substantially axially symmetrical on both sides of the endoscopic observation unit, the fixed parts arranged at least in one of the endoscope and adapter;
    a holder which has a fixing unit to fix removably the fixed parts, and a support unit to support the endoscopic observation unit movably; and
    a grip which is provided in the fixing unit and grips the fixed parts releasably, the grip extended to both sides of the endoscopic observation unit, wherein the adapter has an optical characteristic adjusting means which adjusts optical characteristics, and the optical characteristic adjusting means having a first control unit which is rotated around the insertion axis of the endoscope, and a second control unit which is rotated around the axis in the direction different from the insertion axis.

2. The endoscopic observation apparatus according to claim 1, wherein the optical characteristic adjusting means has a zoom adjusting means which adjusts and operates variable magnification optics which varies the observation magnification of an observation image, and a focus adjusting means which adjusts and operates focusing optics which adjusts the focus of an observation image.

3. The endoscopic observation apparatus according to claim 1, wherein the adapter has an image rotation prism which rotates an optical image obtained by the endoscope, and a holder which holds the image rotation prism rotatable; and the optical characteristic adjusting means has a rotation angle adjusting means which adjusts and operates the image rotation prism.

4. The endoscopic observation apparatus according to claim 1, wherein the fixed parts are substantially cylindrical pins.

5. The endoscopic observation apparatus according to claim 1, wherein the fixing unit has an engagement part which is engaged with the fixed part in the state that at least a part of the endoscopic observation unit is buried in the fixing unit, when the fixed parts are engaged.

6. The endoscopic observation apparatus according to claim 5, wherein the engagement part has a cavity which can contain a part of the endoscope.

7. The endoscopic observation apparatus according to claim 5, wherein the engagement part has a cavity which can contain a part of the adapter.

8. The endoscopic observation apparatus according to claim 5, wherein the engagement part has a cavity which can contain a part of a light guide connected to the endoscopic observation unit.

9. The endoscopic observation apparatus according to claim 5, wherein the engagement part has a cavity which can contain a cable of a control means removable from the endoscopic observation unit.

10. An endoscopic observation apparatus comprising:
    an endoscopic observation unit comprising an endoscope which has an insertion part and an observation axis extending in an insertion direction of the insertion part, the insertion part having a distal end, a base end and an insertion axis, and insertable into a body cavity;
    an adapter which is fit removably to the base end of the endoscope;
    an image pickup camera which is fixed to the endoscope through the adapter, and picks up an image obtained by the endoscope through the adapter, the camera having an image pickup optical axis, wherein the endoscope, adapter and image pickup camera are combined;
    a plurality of fixed parts which are arranged substantially axially symmetrical on both sides of the endoscopic observation unit, the fixed parts arranged at least in one of the endoscope and adapter;

a holder which has a fixing unit to fix removably the fixed parts, and a support unit to support the endoscopic observation unit movably; and a grip which is provided in the fixing unit and grips the fixed parts releasably, the grip extended to both sides of the endoscopic observation unit, wherein the adapter has a refracting means which refracts an optical image obtained by the endoscope in the direction different from the observation optical axis, and guides the image to the image pickup optical axis of the image pickup camera; and an optical characteristic adjusting means which adjusts optical characteristics, and the optical characteristic adjusting means having a plurality of control units, the control units separated and arranged in the observation optical axis side and the image pickup optical axis side with the refracting means interposed therebetween.

* * * * *